United States Patent
Britton

(10) Patent No.: US 8,569,218 B2
(45) Date of Patent: Oct. 29, 2013

(54) CLEANING COMPOSITION CONTAINING POLYMER MICROEMULSION

(75) Inventor: Claudia E. Britton, Aurora, OH (US)

(73) Assignee: Illinois Tool Works, Inc., Glenview, IL (US)

(*) Notice: Subject to any disclaimer, the term of this patent is extended or adjusted under 35 U.S.C. 154(b) by 0 days.

(21) Appl. No.: 13/352,895

(22) Filed: Jan. 18, 2012

(65) Prior Publication Data

US 2012/0231987 A1 Sep. 13, 2012

Related U.S. Application Data

(60) Provisional application No. 61/449,801, filed on Mar. 7, 2011.

(51) Int. Cl.
- *C11D 1/83* (2006.01)
- *C11D 3/18* (2006.01)
- *C11D 3/20* (2006.01)
- *C11D 3/37* (2006.01)

(52) U.S. Cl.
USPC ........... 510/130; 510/127; 510/138; 510/139; 510/153; 510/155; 510/156; 510/403; 510/417; 510/421; 510/426; 510/437; 510/492; 510/505; 424/401; 424/70.19; 424/70.31; 514/937; 514/941; 514/942; 514/943

(58) Field of Classification Search
USPC ......... 510/127, 130, 138, 139, 153, 155, 156, 510/403, 417, 421, 426, 437, 492, 505; 424/401, 70.19, 70.31; 514/937, 941, 514/942, 943
See application file for complete search history.

(56) References Cited

U.S. PATENT DOCUMENTS

| | | | |
|---|---|---|---|
| 5,523,025 A * | 6/1996 | Erilli | 510/417 |
| 5,954,871 A | 9/1999 | Nicolas-Morgantini et al. | |
| 6,066,316 A | 5/2000 | Shiojima et al. | |
| 6,165,962 A * | 12/2000 | Kaler et al. | 510/365 |
| 6,197,734 B1 | 3/2001 | Vlasblom | |
| 6,287,582 B1 | 9/2001 | Gott et al. | |
| 6,645,479 B1 | 11/2003 | Shefer et al. | |
| 7,381,250 B2 | 6/2008 | Hasinovic et al. | |
| 7,393,401 B2 | 7/2008 | Hasinovic et al. | |
| 7,399,479 B2 | 7/2008 | Maillefer et al. | |
| 7,976,624 B2 | 7/2011 | Hasinovic et al. | |
| 2002/0098217 A1 | 7/2002 | Piot et al. | |
| 2003/0059377 A1 | 3/2003 | Riley | |
| 2003/0086951 A9 | 5/2003 | Piot et al. | |
| 2004/0213821 A1 * | 10/2004 | Suginaka et al. | 424/401 |
| 2005/0170988 A1 | 8/2005 | Maillefer et al. | |
| 2006/0002964 A9 | 1/2006 | Schreiber et al. | |
| 2007/0163463 A1 | 7/2007 | Hasinovic et al. | |
| 2007/0163464 A1 | 7/2007 | Hasinovic et al. | |
| 2008/0207778 A1 | 8/2008 | Rodier et al. | |
| 2008/0241089 A1 | 10/2008 | Banowski et al. | |
| 2008/0280797 A1 * | 11/2008 | Compain | 510/136 |
| 2010/0031969 A1 | 2/2010 | Jager Lezer et al. | |
| 2010/0047296 A1 | 2/2010 | Banowski et al. | |

FOREIGN PATENT DOCUMENTS

| | | |
|---|---|---|
| GB | 2 343 189 A | 5/2000 |
| WO | WO 93/15018 A1 | 8/1993 |
| WO | WO 2009/137096 A1 | 11/2009 |

* cited by examiner

*Primary Examiner* — Brian P Mruk
(74) *Attorney, Agent, or Firm* — Blue Filament Law PLLC; Avery N. Goldstein

(57) ABSTRACT

A gelled cleaning composition is provided that includes a standard temperature and pressure (STP) liquid oil or STP malleable wax present from 0.1 to 9.9 total weight percent. An emulsifier is present from 0.01 to 10 total weight percent, along with an alkylene glycol present from 0.002 to 11 total weight percent. A microemulsion is present in the composition from 0.2 to 15 total weight percent. Water forms a majority of the composition such that the composition is monophasic for at least 4 months storage at 20° Celsius. The composition is well suited for use in a process to remove a lipophilic substance from hands or an inanimate substrate by applying the composition and after allow sufficient time for the substance to be softened or solubilized, removing the composition and at least a portion of the substance. Silicone gaskets, as well as other cured resins and paints are readily removed.

15 Claims, No Drawings

CLEANING COMPOSITION CONTAINING POLYMER MICROEMULSION

CROSS-REFERENCE TO RELATED APPLICATIONS

This application is a non-provisional application that claims priority benefit of U.S. Provisional Application Ser. No. 61/449,801, filed Mar. 7, 2011 the contents of which are hereby incorporated by reference.

FIELD OF THE INVENTION

The present invention in general relates to a heavy duty cleaning composition for removal of lipophilic substances such as paints, resins, oily, and organic soils from skin, as well as other surfaces and in particular, to a cleaning composition providing superior storage stability through substitution of some or all of dibasic esters with a polymeric microemulsion.

BACKGROUND OF THE INVENTION

Conventional technology for cleaning paints and resins from surfaces such as the skin utilized a combination of industrial purpose dibasic esters in a hand cleaning compound formulation. These formulations, although effective in removing lipophilic soils, have met with limited acceptance owing to long term storage stability. Over time, dibasic esters tend to hydrolyze into their acid counterparts. This causes the pH and viscosity of a composition containing the same to decrease significantly, causing the composition to become unstable and phase separate. Agitation will render the phase separated composition homogeneous for only a short period of time before it again reverts back to a biphasic state.

Limiting the amount of dibasic esters present in a cleaning composition, while advantageous in reducing overall organic solvent content of a cleaning composition, has proved difficult as a replacement material must prove to be effective against lipophilic soils while retaining stability and precluding skin irritation. Additionally, any substitute for a dibasic ester would ideally also have a reduced ecotoxicity value as measured by an LC50 test per the Organization for Economic Cooperation and Development. While other organic solvents have been evaluated, the solvents have proven to be unable to achieve the disparate requirements for a dibasic ester substitute.

Thus, there exists a need for a cleaning composition substituting a substance for all or part of dibasic esters found in conventional lipophilic soil gelled cleaning compositions with superior storage stability while remaining effective against soils, having a reduced ecotoxicity and skin compatibility.

SUMMARY OF THE INVENTION

A gelled cleaning composition is provided that includes a standard temperature and pressure (STP) liquid oil or STP malleable wax present from 0.1 to 9.9 total weight percent. An emulsifier is present from 0.01 to 10 total weight percent, along with an alkylene glycol that is present from 0.002 to 11 total weight percent. A microemulsion is present in the composition from 0.2 to 15 total weight percent. Water forms a majority of the composition such that the composition is pH stable and monophasic for at least 4 months storage at 20° Celsius.

The composition is well suited for use in a process to remove a lipophilic substance from hands or an inanimate substrate by applying the composition and after allow sufficient time for the substance to be softened or solubilized, removing the composition and at least a portion of the substance. Silicone gaskets, as well as other cured resins and paints are readily removed.

DETAILED DESCRIPTION OF THE PREFERRED EMBODIMENTS

The present invention has utility as a gelled cleaning composition especially well suited for removal of paint, resin, oils, and lipophilic soils. The inventive gelled cleaning composition is particularly well suited as a hand cleaner for removing such substances and soils from a user's skin. An inventive composition is able to replace in part or total, dibasic esters from gelled cleaning compositions for removal of these materials and lipophilic soils with from 1 to 10 total weight percent of a microemulsion to replace in whole or part dibasic esters. The microemulsion in combination with water as a majority material, an oil, a surfactant, an alkylene glycol, and a gellant along with optional additives forms a storage stable gelled cleaning composition. An inventive composition in reducing the quantity of dibasic esters improves the viscosity and pH stability of an inventive formulation relative to conventional gelled cleaning compositions and also performs in a comparable manner to gelled cleaning compositions containing d-limonene. While d-limonene affords an effective material and lipophilic soil removal solvent, d-limonene is known to negatively impact operation of wastewater biodegradation systems.

An inventive gelled composition includes a microemulsion that affords pH storage stability for at least 4 months. pH storage stability is defined as a change in composition pH as measured at standard temperature and pressure that deviates less than one pH unit when the composition is stored at standard temperature and pressure.

The present invention achieves storage stability while maintaining conventional cleaning properties with respect to paints, resins, and other lipophilic soils. Through selection of specific additives, an inventive gelled cleaning composition is readily formulated for topical skin cleaning, a paint stripper, a part degreaser, a brake cleaner, or a substrate preparation material.

The formulary of an inventive gelled cleaning composition is summarized below in Table 1.

TABLE 1

Inventive Gelled Cleaning Composition

| Component | Typical Amount Total Wt. Percent | Preferred Amount - Hand Cleaner Total Wt. Percent | Preferred Amount - Paint Stripper Total Wt. Percent |
|---|---|---|---|
| Liquid oil/malleable wax | 0.1-9.9 | 2-6 | 2-6 |
| Emulsifiers (in total) | 0.1-10 | 1.2-8 | 1.2-8 |
| $C_6$-$C_{12}$ alcohol ethylene oxidepropylene oxide adduct | 0-10 | 0.5-3 | 0.5-3 |
| Polymeric carboxylates | 0-10 | 0.2-2 | 0.2-2 |
| molecular | 0-10 | 0.5-3 | 0.5-3 |
| Alkylene glycol | 0.002-11 | 0.1-9 | 0.1-9 |
| Microemulsion | 0.2-15 | 1.8-6 | 1.8-6 |
| Water | to 100% | to 100% | to 100% |
| Pumice | 0-20 | 2-20 | 0 |
| Lanolin | 0-3 | 0.005-3 | 0 |
| Fragrance | 0-3 | 0.01-3 | 0 |
| Caustic | 0 to pH = 12 | to pH 6-9 | to pH 9 |
| Polyvalent metal ion salt | 0-2 | 0-2 | 0-2 |

TABLE 1-continued

Inventive Gelled Cleaning Composition

| Component | Typical Amount Total Wt. Percent | Preferred Amount - Hand Cleaner Total Wt. Percent | Preferred Amount - Paint Stripper Total Wt. Percent |
| --- | --- | --- | --- |
| Antimicrobial | 0-2 | 0.005-1 | 0.005-1 |
| Foaming agent | 0-2 | 0-0.6 | 0 |
| Polar organic solvent | 0-5 | 0.1-3 | 0.1-3 |
| DBE | 0.2< | 0.2< | 0.2< |

It is appreciated that regardless of the specifics of a given formulation, an inventive composition has the property of pH storage stability as well as homogeneity retention through inclusion of a microemulsion for a time period of at least 4 months.

An inventive composition includes an oil that is liquid at standard temperature and pressure (STP of 25° Celsius, 760 torr) or a wax that is malleable at STP. An oil or room temperature wax herein is only limited by the requirement that the oil or wax selected be compatible and substantially nonreactive with other composition components. "Substantially nonreactive" as defined herein is used throughout as meaning formation of covalent bonds with other composition constituents to a degree of less than 1 mole percent. Oils and waxes operative herein illustratively include mineral oil; petrolatum; natural oils such as soybean, rapeseed, castor ben oil (ben), sunflower, peanut, cottonseed, palm kernel, coconut, corn, linseed, and safflower; waxes such as paraffin, and beeswax; hydrogenated forms thereof; methoxylated forms thereof; ethoxylated forms thereof; and combinations thereof. An oil or wax component of an inventive formulation is typically present from 0.1 to 9.9 total weight percent, with 2 to 6 total weight percent being preferred. Without intending to be bound by a particular theory, it is believed that the oil or wax component facilitates solubilization of the target lipophilic soil, resin paint, or other residue.

An inventive composition includes one or more emulsifiers to promote phase homogeneity and stability thereof for an inventive composition. It is appreciated that the emulsifiers also have a role in lifting the solubilization of a target soil, resin, or other substance disintegration into a soluble or colloidal form within an inventive composition. Emulsifiers operative herein are operatively limited only in being chemically compatible and substantially nonreactive with other components of an inventive composition and in quantities required to retain pH storage stability and phase homogeneity. Types of emulsifiers operative herein include $C_6$-$C_{12}$ alcohol ethoxide-propoxide (EOPO) adducts, polymeric carboxylates, and molecular emulsifiers. It is appreciated that the overall loadings of emulsifiers of the present invention and combinations thereof are somewhat variable based on specific identities in order to retain stability of inventive gelled cleaning compositions; however, factors relevant in selecting the quantity of emulsifiers include quantity of microemulsion present, composition viscosity, molecular weight of oil and/or wax present. Specific examples of alkyl alcohol alkoxide adduct emulsifiers illustratively include $C_8$-$C_{10}$ alcohol ethoxide-propoxide adducts commercially available under the trade name GENAPOL® with molecular weights between 800 and 4000. Polymeric carboxylates operative as emulsifiers include polymers of acrylic acid crosslinked with polyalkenyl ethers or divinyl glycols and are commercially known as "CARBOPOLs®". Typical CARBOPOL® polymer particulate have dimensions of between 0.2 and 6 microns average diameter and are characterized as being flocculated agglomerates. It is appreciated that polymers are available that vary in total molecular weight, molecular weight between cross links, and as a result vary in viscosity and water swell properties per gram of CARBOPOL® polymer. Molecular emulsifiers characterized by a molecular weight of generally less than about 500 atomic mass units include aliphatic sequences as well as hydrophilic substituents such as one or more of the moieties of hydroxyl, carboxylate, quaternary amine, and sulfonate. A molecular emulsifier operative herein illustratively includes triethanolamine, cetyl stearyl alcohol, sorbitan sesquioleate, polyoxyethylene sorbitan monopalmitate, polyoxyethylene sorbitan monooleate, non-ethoxylated glyceryl monostearate, cetearyl alcohol, sodium stearoyl lactylate, lecithin, and combinations thereof. Typically, a molecular emulsifier is present from 0.5 to 3 total weight percent. Preferably, an emulsifier package is provided that includes a CARBOPOL® emulsifier as well as at least one molecular emulsifier. More preferably, an adduct type emulsifier is present along with a CARBOPOL® emulsifier and a molecular emulsifier. Representative ranges of the emulsifiers adduct type: CARBOPOL® emulsifier: molecular emulsifier are on a weight basis 01-0.4: 0.06-0.20:1 and in an exemplary formulation.

An inventive composition also includes an alkylene glycol or polymer formed thereof. An inventive alkylene glycol is ethylene glycol, propylene glycol, a combination thereof, polyethylene glycol, polypropylene glycol, a mixed poly(ethylene glycol-propylene glycol), and a combination thereof. Typical quantities of an alkylene glycol present in the present invention range from 0.002-11 total weight percent, with 0.1-9 total weight percent being preferred.

The inventive composition constituents of an oil/malleable wax, emulsifiers, and alkylene glycol form a pH stable gelled composition that resists phase separation for at least 4 months with inclusion of a microemulsion present at a total weight percent of between 0.3 and 15 percent and preferably, between 1.8 and 6 total weight percent, with water and optional additives thereto constituting the remaining percentage of the composition. A microemulsion is preferably premixed and provided as a concentrate that is intermixed with the remaining composition constituents. A microemulsion operative herein includes an anionic surfactant that is water soluble and non-soaping; and includes an organic hydrophobic group containing between 8 and 26 carbon atoms and preferably, between 8 and 20 aliphatic carbons along with at least one hydrophilic moiety of hydroxyl, sulfonate, sulfate, or carboxylate. Hydrophobic portion of molecule typically includes a $C_8$-$C_{22}$-alkyl, -aryl, or -acyl group. The surfactants are present as salts along with salt forming cation common to the art. Non-soaping anionic surfactants operative herein illustratively include linear alkyl benzene sulfonates, olefin sulfonates, hydroxyl alkane sulfonates, paraffin sulfonates, ethoxylated $C_8$-$C_{24}$ alkyl ether sulfates, and di($C_1$-$C_8$ alkyl) sulfosuccinates, and combinations thereof. In addition to the nonsoaping water soluble anionic surfactant, the microemulsion component of an inventive composition is intermixed with a polar organic molecule, the polar organic molecule having a hydrophobic aliphatic portion and at least one hydrophilic moiety. Typically, the molecular weight of a polar organic component of a microemulsion is between 50 and 500 atomic mass units. It is also appreciated that molecular emulsifiers as detailed above are also operative herein as the polar organic component of a microemulsion component. In addition to the molecular emulsifiers, a polar organic operative in an inventive composition illustratively includes $C_2$-$C_{14}$ diols; dibasic esters such as $C_1$-$C_6$ esters of adipic, glutaric and succinic acids; and combinations thereof. Preferably, the non-soaping anionic surfactant is intermixed with at least two different types of polar organics in the presence of a majority phase water to form a microemulsion. Representative formulations and techniques for formation of microemulsions are illustratively detailed in U.S. Pat. No. 5,523,025 and U.S. Pat. No. 6,165,962. Optionally, terpenes or terpenoids are added to the microemulsion to facilitate removal of soil, and lipophilic resin or debris. Terpenes and terpenoids suitable for inclusion in a microemulsion illustratively include limonene, and turpentine spirits. An inventive microemulsion is readily formed by mixing together between 20-60 microemulsion total weight percent polar organics, 20-60 microemulsion total weight percent water, 5-30 percent anionic surfactant, and optionally between 0-20 percent terpene, terpenoids or a combination thereof The resultant microemulsion after formation is added to an inventive gelled cleaning composition in an amount of between 0.3-15 total composition weight percent and preferably between 1.86 total weight percent of the inventive composition.

A base gelled composition inclusive of the oil/malleable wax, alkylene glycol, emulsifiers, and microemulsion with the remainder being water is itself effective to remove or soften cured paints, varnishes, resins, and silicones. It is appreciated that a base inventive composition is readily modified through the inclusion of optional additives to afford usage specific benefits such as those of a hand cleaner or a stripping gel.

Optional additives to a base inventive composition that are well suited for the formation of a gelled hand cleaning composition include an abrasive such as pumice, carborundum, sand, or combinations thereof in amounts typically between 2 and 20 total weight percent; an emollient such as lanolin, petrolatum, vitamin E oil, aloe vera, or jojoba, present in quantities between 0.005 and 3 total weight percent; fragrance compounds typically present from 0.001 to 3 total percent; polyvalent metal ion salts such as magnesium oxide, magnesium sulfate, magnesium hydroxide, magnesium chloride, magnesium carboxylates, magnesium halides, or magnesium nitrates, as well as aluminum, iron, calcium, and other polyvalent metal ions forming salts with these anions, the polyvalent metal ion salts are typically present from 0 to 2 total weight percent and are well suited for improving lipophilic soil lift in water containing higher salt loadings; an antimicrobial to improve storage stability that illustratively includes quaterniums, and other conventional antibacterials, an antimicrobial typically being present from 0 to 2 total weight percent and preferably between 0.005 and 1 total weight percent; a foaming agent present from 0 to 2 total weight percent and preferably, between 0.2 and 0.6 total weight percent (if present); dibasic esters typically present between 0 and less than 0.4 total weight percent and preferably, present at less than 0.2 total weight percent; a colorant present in an amount of from 0 to 1 total weight percent and preferably, from 0 to 0.3 total weight percent; and a pH modifying source of a mineral acid, organic acid, or hydroxide source such as sodium hydroxide or potassium hydroxide, a pH buffer such as EDTA or salts thereof, with the pH modifier being present in a quantity appropriate to adjust overall inventive composition pH to a desired value while preserving pH storage stability and phase stability thereof. Typical pH values range from pH 6 to 12 fully formulated, and preferably pH 6 to 9.

The present invention is further detailed with respect to the following nonlimiting examples. Unless otherwise specified, the percentages detailed herein are total weight percent of the inventive formulation.

Example 1

To 500 milliliters of municipal water is added sequentially 1.2 grams of triethanolamine, 0.5 grams of CARBOPOL®-1382, 1.8 grams of a $C_8$-$C_{10}$ alcohol EOPO adduct sold under the trade name GENAPOL®-2222, and 0.9 grams of propylene glycol. 3.5 grams of a microemulsion is then added, the microemulsion being composed of 20 emulsion percent sodium di(hexyl)sulfosuccinate, 40 percent dibasic esters, and 10 microemulsion weight percent of polyethylene glycol (MW 200), with the remainder being water. With addition of the emulsion, additional components are added including quaternium-15 at 0.1 grams; 0.25 grams fragrance; 4 grams of mineral oil; 8 grams of pumice; and trace amounts of lanolin, aloe vera, vitamin E oil, and jojoba oil. The volume is brought to approximately 1 liter with the addition of 295 additional grams of municipal water and the mixture is stirred at 20° Celsius until homogeneous. The resultant composition constitutes an effective gelled hand cleaner able to solubilize or otherwise lift more than 0.1 grams petroleum jelly per gram of inventive gelled hand cleaner composition from hands with 2 minutes of interworking to user hands followed by a warm water rinse.

After 4 months of storage at 20° Celsius, the pH is noted to be within 0.5 units of as-formulated pH and the inventive composition remains a monophasic gel.

Example 2

The gelled cleaning composition of Example 1 is reformulated with dodecyl benzene sulfonate in place of the sulfosuccinate in the emulsion with the emulsion being present in the inventive formulation at an amount of 3 total weight percent. 0.7 grams of CARBOPOL-934 is used in lieu of the CARBOPOL detailed above in Example 1 with the quantity of water being adjusted to compensate for differential in other components. A gelled cleaning composition with similar properties to that of Example 1 is produced.

Example 3

To 500 milliliters of municipal water is added sequentially 1.2 grams of triethanolamine, 0.5 grams of CARBOPOL 1382, 1.8 grams of a $C_8C_{10}$ alcohol EOPO adduct sold under the trade name GENAPOL®-2222, and 0.9 grams of propylene glycol. 3.5 grams of a microemulsion is then added, the microemulsion being composed of 20 emulsion percent sodium di(hexyl)sulfosuccinate, 40 percent dibasic esters, and 10 microemulsion weight percent of polyethylene glycol (MW 200), with the remainder being water. With addition of the emulsion, additional components are added including quaternium-15 at 0.1 grams; 0.25 grams fragrance; and 4 grams of mineral oil. The volume is brought to approximately 1 liter with the addition of municipal water and the mixture is stirred at 20° Celsius until homogeneous. The resultant composition constitutes an effective gelled silicone gasket remover able to soften or otherwise lift more than 0.2 grams of RTV silicone per gram of inventive gelled silicone gasket composition after 10 minutes of contact.

After 4 months of storage at 20° Celsius, the pH is noted to be within 0.3 pH units of the as-formulated inventive composition and remains a monophasic gel.

Example 4

The gelled cleaning composition of Example 3 is reformulated with ethoxylated $C_{12}$ alkyl ether sulfate in place of the sulfosuccinate in the microemulsion with the microemulsion being present in the inventive formulation at an amount of 2.2 total weight percent. A gelled cleaning composition with similar properties to that of Example 3 is produced.

Patent documents and publications mentioned in the specification are indicative of the levels of those skilled in the art to which the invention pertains. These documents and publications are incorporated herein by reference to the same extent as if each individual document or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

The invention claimed is:

1. A storage stable gelled cleaning composition comprising:
    a liquid oil or a malleable wax present from 0.1 to 9.9 total weight percent;
    an emulsifier present from 0.01 to 10 total weight percent;
    an alkylene glycol present from 0.002 to 11 total weight percent;
    a microemulsion present from 0.2 to 15 total weight percent;
    an abrasive or a skin emollient or a combination thereof; and
    water forming a majority of the composition, the composition remaining monophasic for at least 4 months storage at 20° Celsius.

2. The composition of claim 1 wherein said emulsifier includes at least one of a $C_6$-$C_{12}$ alcohol ethylene oxide-propylene oxide adduct, a polymeric carboxylates, or a molecular emulsifier with molecular weight of 500 or less atomic mass units.

3. The composition of claim 2 wherein said emulsifier comprises at least one said adduct and at least one of said polymeric carboxylate.

4. The composition of claim 2 wherein said emulsifier comprises at least one of said molecular emulsifier and at least one of said polymeric carboxylate.

5. The composition of claim 2 wherein said emulsifier comprises at least one of said adduct, at least one of said polymeric carboxylate, and at least one of said molecular emulsifier.

6. The composition of claim 1 wherein said microemulsion is present from 0.3 to 1 total weight percent.

7. The composition of claim 1 wherein said abrasive is present.

8. The composition of claim 1 wherein said skin emollient is present.

9. The composition of claim 1 further comprising a pH additive to achieve a pH for the composition of between 6 and 9.

10. The gelled composition of claim 1 further comprising a polyvalent metal ion salt.

11. The composition of claim 1 wherein said microemulsion comprises a dibasic ester; water; a polar organic solvent; and an anionic surfactant that is a sulfonate, sulfate, or phosphonate.

12. The composition of claim 11 wherein said anionic surfactant is a sulfosuccinate.

13. The composition of claim 11 wherein said polar organic solvent comprises at least one of a dibasic ester, $C_2$-$C_{14}$ diol, or a combination thereof.

14. A process for cleaning hands comprising:
    applying a storage stable composition comprising: a liquid oil or a malleable wax present from 0.1 to 9.9 total weight percent; an emulsifier present from 0.01 to 10 total weight percent; an alkylene glycol present from 0.002 to 11 total weight percent; a microemulsion present from 0.2 to 15 total weight percent; at least one of an abrasive present from 2 to 20 total weight percent or a skin emollient present from 0.005 to 3 total weight percent; and water forming a majority of the composition, the composition remaining monophasic for at least 4 months storage at 20° Celsius;
    allowing sufficient time for the composition to interact with a lipophilic substance on the hands; and
    removing the composition and a portion of said lipophilic substance from the hands.

15. A process for cleaning an inanimate substrate coated with a lipophilic substance comprising:
    applying a storage stable composition to the lipophilic substance, the composition comprising: a liquid oil or a malleable wax present from 0.1 to 9.9 total weight percent; an emulsifier present from 0.01 to 10 total weight percent; an alkylene glycol present from 0.002 to 11 total weight percent; a microemulsion present from 0.2 to 15 total weight percent; at least one of an abrasive present from 2 to 20 total weight percent or a skin emollient present from 0.005 to 3 total weight percent; and water forming a majority of the composition, the composition remaining monophasic for at least 4 months storage at 20° Celsius;
    allowing sufficient time for the composition to interact with a lipophilic substance on the substrate; and
    removing the composition and a portion of said lipophilic substance from the substrate.

* * * * *